(12) United States Patent
Woelfert et al.

(10) Patent No.: US 8,258,337 B2
(45) Date of Patent: Sep. 4, 2012

(54) METHOD FOR PRODUCING ISOCYANATES

(75) Inventors: Andreas Woelfert, Bad Rappenau (DE); Carsten Knoesche, Niederkirchen (DE); Andreas Daiss, Deidesheim (DE); Tsung-Chieh Cheng, Heppenheim (DE); Torsten Mattke, Freinsheim (DE); Eckhard Stroefer, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 808 days.

(21) Appl. No.: 12/065,964

(22) PCT Filed: Aug. 23, 2006

(86) PCT No.: PCT/EP2006/065593
§ 371 (c)(1),
(2), (4) Date: Mar. 6, 2008

(87) PCT Pub. No.: WO2007/028715
PCT Pub. Date: Mar. 15, 2007

(65) Prior Publication Data
US 2009/0221846 A1    Sep. 3, 2009

(30) Foreign Application Priority Data
Sep. 6, 2005 (DE) .......................... 10 2005 042 392

(51) Int. Cl.
*C07C 263/00* (2006.01)

(52) U.S. Cl. ......... 560/347; 560/330; 560/336; 560/338

(58) Field of Classification Search .................. None
See application file for complete search history.

(56) References Cited

U.S. PATENT DOCUMENTS

| 6,930,199 B2 * | 8/2005 | Meyn et al. | 560/347 |
| 6,974,880 B2 * | 12/2005 | Biskup et al. | 560/347 |
| 2005/0222453 A1 * | 10/2005 | Woelfert et al. | 560/347 |

FOREIGN PATENT DOCUMENTS

| DE | 103 59 627 | 7/2005 |
| EP | 1 275 639 | 1/2003 |
| EP | 1 275 640 | 1/2003 |
| EP | 1 449 826 | 8/2004 |
| EP | 1 555 258 | 7/2005 |
| WO | 02 02217 | 1/2002 |

OTHER PUBLICATIONS

U.S. Appl. No. 12/446,460, filed Apr. 21, 2009, Boehling, et al.
U.S. Appl. No. 12/675,137, filed Feb. 25, 2010, Olbert, et al.
U.S. Appl. No. 12/675,187, filed Feb. 25, 2010, Olbert, et al.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

The present invention relates to a process for preparing isocyanates and an apparatus suitable for this purpose, and also its use. In the process, an amine and phosgene, both in the gas phase, react in the presence of an inert medium. A number, n, of amine streams are reacted with a number, n +1, of phosgene streams in a reactor. The number n is a positive integer of at least 1. All amine and phosgene streams are introduced into the reactor through annular gaps for mixing.

23 Claims, 2 Drawing Sheets

METHOD FOR PRODUCING ISOCYANATES

CROSS-REFERENCE TO RELATED APPLICATIONS

The present application is a National Stage of International Application No. PCT/EP06/65593, filed on Aug. 23, 2006. This application claims the benefits of priority to German Patent Application No. 10 2005 042 392.2, filed on Sep. 6, 2005.

BACKGROUND OF THE INVENTION

The present invention relates to a process for preparing isocyanates and an apparatus suitable for this purpose, and also its use.

To prepare isocyanates by phosgenation of the corresponding amines, there is in principle a choice between a liquid-phase phosgenation and a gas-phase phosgenation. In the gas-phase phosgenation, the reaction conditions are selected so that at least the reaction components diamine, diisocyanate and phosgene are gaseous under these conditions. The present invention relates exclusively to gas-phase phosgenation.

EP 1 275 639 A1 describes the gas-phase phosgenation of (cyclo)aliphatic diamines in a reaction zone having constrictions of the walls.

EP 1 275 640 A1 describes the gas-phase phosgenation of (cyclo)aliphatic diamines and triamines in a mixing tube with reactor, in which the gas flow is accelerated in the mixing region. A reactor geometry having an inner tube and an outer tube, by means of which a gas-phase phosgenation is possible only on a scale of about 211 g of 1,6-hexamethylenediamine per hour, is disclosed.

A disadvantage of the reactors disclosed in these two documents is that if this reactor geometry were simply to be enlarged to industrially useful sizes, the diameter of the inner tube would have to be increased to such an extent that mixing of the streams introduced through the two tubes would no longer possible in short mixing times owing to the long distances transverse to the flow direction.

EP 1 449 826 A1 discloses a predistribution of the amine-comprising stream over at least two individual amine lines. However, these are hydrodynamically decoupled from one another. If the cross section of one of these tubes is reduced for example by formation of amine hydrochlorides, the throughput through this tube automatically becomes smaller due to the increase in the pressure drop and leads to reduced flow. However, smaller throughputs lead to even more solids depositing on the wall, so that blocking of the tube proceeds even faster.

DE 10359627 A1 discloses a gas-phase phosgenation in which amine is mixed in through a concentric annular gap between two phosgene streams, with the cross-sectional areas of the two phosgene streams having a ratio of from 1:0.5 to 1:4.

This reactor geometry, too has the disadvantage that when this reactor geometry is simply enlarged to industrially useful size, the internal diameter of the mixing device can be increased only up to a particular limit in order for this area ratio to be adhered to.

WO 02/02217 describes various methods of mixing feed streams, including streams for a liquid-phase phosgenation.

A disadvantage is that the methods disclosed there are intended for the mixing of liquid phases at low entry velocities of only about 10 m/s, while the significantly higher velocities and the mixing of gases required in gas-phase phosgenations are subject to different fluid-dynamic requirements than the mixing of liquids. In addition, the reaction rates of a phosgenation in the gas phase are significantly different from those in the liquid phase, so that the method of WO 02/02217 cannot be readily applied to the gas phase.

It was an object of the present invention to develop a method for carrying out a gas-phase phosgenation which can be implemented on an industrial scale.

BRIEF SUMMARY OF THE INVENTION

This object is achieved by a process for preparing isocyanates by reacting the corresponding amines with phosgene, if appropriate in the presence of at least one inert medium, in the gas phase, in which n amine streams are reacted with n+1 phosgene streams in a reactor, where n is a positive integer of at least 1, and all amine and phosgene streams are introduced into the reactor via annular gaps for mixing.

DETAILED DESCRIPTION OF THE INVENTION

In this text, the terms "annular gap" and "annular gap space" are used as follows:

The annular gap space is to be understood as a generalization of a hollow cylinder (for the definition of a hollow cylinder, see Bronstein, "Taschenbuch der Mathematik", 21 st edition, p. 199): an annular gap space is a volume which is enclosed by an outer curved surface and an inner curved surface, which are each closed, and the delimiting end faces, with the two curved surfaces not penetrating one another.

The annular gap is understood as a generalization of a circular area (for the definition of a circular area, see Bronstein, "Taschenbuch der Mathematik", 21st edition, p. 194): the annular gap has the shape of an end face which delimits the above-described annular gap space at its end face.

Figure 1:
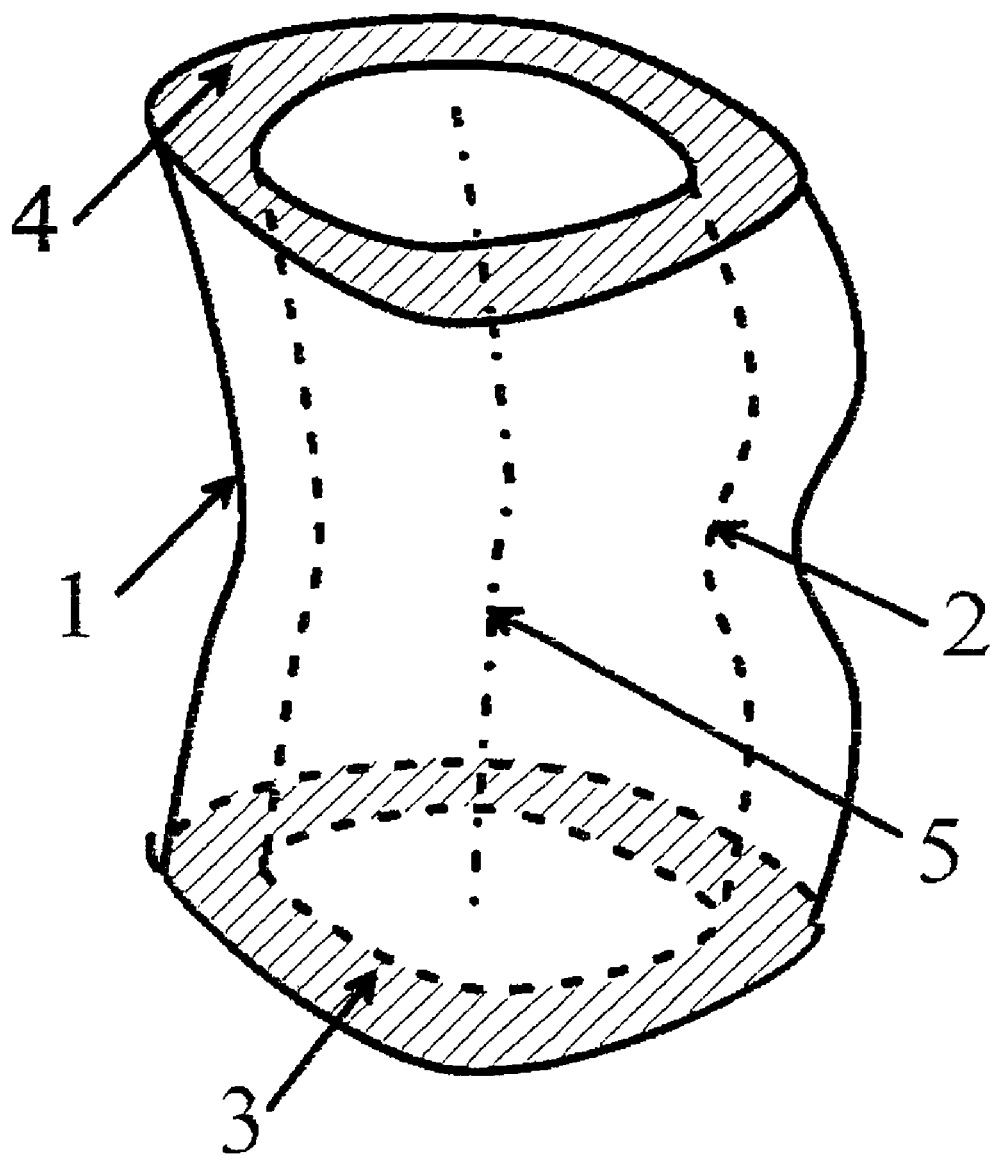
FIG. 1 shows a generalization of an annular gap space.

The annular gap space (see FIG. 1) has a longitudinal axis 5 even in the case of an irregular shape. To construct this longitudinal axis 5, a point is selected in the interior of the inner curved surface 2 and the plane which comprises this point and forms a section across the annular gap space which has the lowest section area but is completely in the form of an annular gap is located. The center of gravity of this annular-gap-shaped section across the annular gap space is located on the longitudinal axis of the annular gap space. Further points on the longitudinal axis 5 can be determined using the same procedure and selecting other points in the interior of the inner curved surface 2. The longitudinal axis 5 is made up of the totality of all centers of gravity of such sections. The longitudinal axis preferably forms a straight line.

The phosgene- and amine-comprising feed streams to be introduced into the annular gap space in the process enter the annular gap space at one end through (2n+1), for example three, annular-gap-shaped areas. These annular gaps are arranged relative to one another so that their centers of gravity are located essentially on a straight line, with the center of gravity of the annular gap which projects furthest into the annular gap space being located on the longitudinal axis of the annular gap space.

The centers of gravity of the annular gaps used for introduction of the feed streams are preferably located at one point, so that the areas are arranged concentrically. The totality of all annular gaps used for introduction of the feed streams, including the struts located between them, then form an annular gap which represents one of the two end faces of the annular gap space.

"Rotationally symmetric" means that a body, here the annular gap space, or an area, here the associated annular gap, has rotational symmetry when rotated about the rotational axis. The axis of symmetry can be, for example, a two-fold rotational axis $C_2$, a three-fold axis $C_3$ or a four-fold rotational axis $C_4$ or preferably an axis of full rotational symmetry ($C_\infty$). Thus, for example, a flat annular gap bounded by two ellipses having coincident longitudinal and transverse main axes has a two-fold rotational axis. As a further example, a circular annulus has full rotational symmetry.

The amines which can be used in a gas-phase phosgenation have to meet particular requirements (see below).

They can be monoamines, diamines, triamines or amines having a higher functionality, preferably diamines. Accordingly, the corresponding monoisocyanates, diisocyanates, triisocyanates or isocyanates having a higher functionality, preferably diisocyanates, are formed.

The amines and isocyanates can be aliphatic, cycloaliphatic or aromatic, preferably aliphatic or cycloaliphatic and particularly preferably aliphatic.

Cycloaliphatic isocyanates are isocyanates which comprise at least one cycloaliphatic ring system.

Aliphatic isocyanates are isocyanates which have only isocyanate groups which are bound to straight or branched chains.

Aromatic isocyanates are isocyanates which have at least one isocyanate group bound to at least one aromatic ring system.

For the purposes of the present patent application, the term "(cyclo)aliphatic isocyanates" is used as an abbreviation for cycloaliphatic and/or aliphatic isocyanates.

Examples of aromatic diisocyanates are preferably those having 6-20 carbon atoms, for example monomeric 2,4'- or 4,4'-methylenedi(phenyl isocyanate) (MDI), tolylene 2,4- and/or 2,6-diisocyanate (TDI) and naphthylene 1,5- or 1,8-diisocyanate (NDI).

Diisocyanates are preferably (cyclo)aliphatic diisocyanates, particularly preferably (cyclo)aliphatic diisocyanates having from 4 to 20 carbon atoms.

Examples of customary diisocyanates are aliphatic diisocyanates such as tetramethylene 1,4-diisocyanate, hexamethylene diisocyanate (1,6-diisocyanatohexane), octamethylene 1,8-diisocyanate, decamethylene 1,10-diisocyanate, dodecamethylene 1,12-diisocyanate, tetradecamethylene 1,14-diisocyanate, derivatives of lysine diisocyanate, tetramethylxylylene diisocyanate (TMXDI), trimethylhexane diisocyanate or tetramethylhexane diisocyanate, and 3 (or 4), 8 (or 9)-bis(isocyanatomethyl)tricyclo[5.2.1.0$^{2,6}$]decane isomer mixtures and also cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanatomethyl)cyclohexane, 2,4-, or 2,6-diisocyanato-1-methylcyclohexane.

Preference is given to 1,6-diisocyanatohexane, 1-isocyanato-3,3,5-trimethyl-5-(isocyanatomethyl)cyclohexane, 4,4'-di(isocyanatocyclohexyl)methane and tolylene diisocyanate isomer mixtures. Particular preference is given to 1,6-diisocyanatohexane, 1-isocyanato-3,3,5-trimethyl-5-(isocyanatomethyl)cyclohexane and 4,4'-di(isocyanatocyclohexyl)methane.

In the process of the invention, amines which can be used for the reaction to form the corresponding isocyanates are ones where the amine, the corresponding intermediates and the corresponding isocyanates are gaseous under the reaction conditions selected. Preference is given to amines which under the reaction conditions decompose to an extent of not more than 2 mol %, particularly preferably not more than 1 mol % and very particularly preferably not more than 0.5 mol %, during the duration of the reaction. Particularly suitable amines here are amines, in particular diamines, based on aliphatic or cycloaliphatic hydrocarbons having from 2 to 18 carbon atoms. Examples are 1,6-diaminohexane, 1-amino-3,3,5-trimethyl-5-aminomethylcyclohexane (IPDA) and 4,4'-diaminodicyclohexylmethane. Preference is given to using 1,6-diaminohexane (HDA).

It is likewise possible to use aromatic amines which can be brought into the gas phase without significant decomposition for the process of the invention. Examples of preferred aromatic amines are toluenediamine (TDA) as the 2, 4 or 2,6 isomer or as a mixture thereof, for example as a 80:20-65:35 (mol/mol) mixture, diaminobenzene, 2,6-xylidine, napthalenediamine (NDA) and 2,4'- or 4,4'-methylenedi(phenylamine) (MDA) or isomer mixtures thereof. Among these, preference is given to the diamines, and particular preference is given to 2,4- and/or 2,6-TDA.

In the gas-phase phosgenation, it should, by definition, be the case that the compounds occurring during the reaction, i.e. starting materials (diamine and phosgene), intermediates (in particular the monocarbamoyl and dicarbamoyl chlorides formed as intermediates), end products (diisocyanate) and any inert compounds introduced, remain in the gas phase under the reaction conditions. Should these or other components separate out from the gas phase and, for example, deposit on the reactor wall or other parts of the apparatus, these deposits can influence heat transfer or flow through the components concerned in an undesirable way. This applies particularly to amine hydrochlorides which are formed from free amino groups and hydrogen chloride (HCl), since the resulting amine hydrochlorides precipitate easily and can be vaporized again only with difficulty.

The starting materials, or only one of them, can be fed into the mixing space together with at least one inert medium.

The inert medium is a medium which is present in the reaction space in gaseous form at the reaction temperature and does not react with the compounds occurring during the course of the reaction. The inert medium is generally mixed with amine and/or phosgene prior to the reaction, but can also be introduced separately from the feed streams. For example, nitrogen, noble gases such as helium or argon, or aromatics such as chlorobenzene, chlorotoluene, o-dichlorobenzene, toluene, xylene, chloronaphthalene, decahydronaphthalene, carbon dioxide or carbon monoxide can be used. Preference is given to using nitrogen and/or chlorobenzene as inert medium.

In general, the inert medium is used in such an amount that the ratio of the gas volumes of inert medium to amine or to phosgene is from >0.0001 to 30, preferably from >0.01 to 15, particularly preferably from >0.1 to 5.

Before carrying out the process of the invention, the starting amines are vaporized and heated to from 200° C. to 600° C., preferably from 300° C. to 500° C., and, if appropriate, diluted with an inert gas or fed into the reactor through the mixing device together with the vapor of an inert solvent Before carrying out the process of the invention, the phosgene used in the phosgenation is, if appropriate, diluted with an inert gas or with the vapor of an inert solvent and likewise heated to a temperature in the range from 200° C. to 600° C., preferably from 300° C. to 500° C.

In a preferred embodiment, the n amine streams are heated to a temperature which is up to 50° C. higher than that of the (n+1) phosgene streams, preferably to a temperature which is up to 30° C. higher, particularly preferably up to 24° C. higher and very particularly preferably up to 20° C. higher. The temperature of the n amine streams is preferably at least 5° C., particularly preferably at least 10° C., higher than that of the (n+1) phosgene streams.

According to the invention, phosgene is used in an excess over amino groups. The molar ratio of phosgene to amino groups is usually from 1.1:1 to 20:1, preferably from 1.2:1 to 5:1.

In the process of the invention, the mixing and reaction of the two gaseous starting materials takes place in the annular gap space as reaction space after introduction of the feed streams diamine and phosgene via the annular gaps as entrance areas.

The reaction generally commences on contact of the starting materials immediately after mixing.

Thus, mixing of starting materials, if appropriate mixed with inert medium, takes place in the front part of the reaction space (mixing space).

To carry out the reaction according to the invention, the preheated stream comprising amine or mixtures of amines and the preheated stream comprising phosgene are introduced continuously into the reactor, preferably a tube reactor.

The reactors generally comprise steel, glass, alloy steel or enameled steel and have a length which is sufficient to allow complete reaction of the diamine with the phosgene under the process conditions.

Mixing Device

The (n+1) phosgene streams and n amine streams are generally fed into a residence reactor via a mixing unit at one end of the reactor. An amine stream is fed in at high velocity through an annular gap between 2 phosgene streams. All phosgene streams and amine streams are introduced via annular gaps. The annular gaps through which adjacent phosgene streams and the amine stream located in between are introduced are preferably ones whose centers of gravity of their areas are located on a straight line, particularly preferably ones whose centers of gravity of their areas coincide at one point.

The streams are very particularly preferably introduced through rotationally symmetric annular gaps.

The annular gaps can have any shape. Conceivable shapes are irregular shapes, trapezoidal, rectangular, square, polygonal, oval, ellipsoidal or circular annular gaps, preferably rectangular, square, oval, ellipsoidal or circular and particularly preferably circular annular gaps. The shape of the annular gap spaces is generally also determined by the shape of the annular gaps. However, it is also conceivable, although less preferred, for the annular gap spaces to have shapes different from the annular gaps.

It can be useful to install flow equalizers as are known, for example, from EP 1362847 in the feed lines. However, a preliminary section in the feed line which has a length greater than the diameter of the feed line and has a diameter which is from 2 to 40 times, particularly preferably from 4 to 30 times, very particularly preferably from 5 to 20 times, the diameter of the feed line is preferably used for equalizing the velocity of the feed streams.

According to the invention, a very small transverse diffusion stretch over which the fluid elements are exchanged by turbulent and laminar diffusion and thus effect mixing is critical for mixing of the streams. While in DE 103 59 627 A1 the amine stream is introduced via a double-walled guide tube which forms an annular gap, only the outer of the two phosgene streams is introduced via an annular gap, namely via a "cross-sectional area which is bounded by the wall of the tube reactor and the outer wall of the double-walled guide tube", whereas the inner phosgene stream is introduced via the "cross-sectional area which is bounded by the inner wall of the double-walled guide tube", i.e. via a circular area. Thus, according to the teachings of DE 103 59 627 A1, an enlargement of the cross section of the reactor or of the inner phosgene feed rate leads to an increase in the transverse diffusion stretch between the inner phosgene stream and the amine stream.

According to the invention, the amine stream is mixed via an annular gap between two phosgene streams which are in turn introduced via annular gaps. This inventive principle can be generalized analogously for the introduction of n amine streams, for example 2, 3, 4 or more, between, in each case, two layers of (n+1) phosgene streams.

n is preferably 1, 2 or 3, particularly preferably 1 or 2 and very particularly preferably 1.

For the innermost phosgene stream to be able, according to the inventive concept, to be introduced via an annular gap, the interior of the annular gap and of the subsequent annular gap space is filled out by a volume body or displacer as core, which extends from the end face of the reaction space into the reaction space.

This results, according to the invention, in the innermost stream and the outermost stream each being a phosgene stream which keeps the amine stream or streams away from the walls of the reactor, both from the outer wall and from the internal volume body.

The ratio of the total area of the amine streams to the total area of the phosgene streams is greater than 0.00002, preferably greater than 0.0002, particularly preferably greater than 0.002 and very particularly preferably greater than 0.02.

The ratio of the total area of the amine streams to the total area of the phosgene streams is less than 5, preferably less than 1, particularly preferably less than 0.5 and very particularly preferably less than 0.2.

The area ratio of two phosgene-conveying annular gaps which are separated by an amine-conveying annular gap is from 0.1 to 10, preferably from 0.2 to 5, particularly preferably from 0.4 to 2.5, very particularly preferably from 0.8 to 1.25, in particular from 0.9 to 1.1 and especially 1.

When $n \geq 2$, the area ratio of two amine-conveying annular gaps which are separated by a phosgene-conveying annular gap is from 0.1 to 10, preferably from 0.2 to 5, particularly preferably from 0.4 to 2.5, very particularly preferably from 0.8 to 1.25, in particular from 0.9 to 1.1 and especially 1.

The individual starting materials are conveyed in the mixing device at a flow velocity of from 20 to 400 meter/second, preferably from 25 to 300 meter/second, particularly preferably from 30 to 250 meter/second, very particularly preferably from 50 to 200 meter/second, in particularly from >150 to 200 meter/second and especially from 160 to 180 meter/second, into the reactor.

In one possible embodiment of the invention, it can be useful to introduce the phosgene streams, in particular the outer phosgene stream, through the annular gap into the mixing space at a higher flow velocity than the amine stream which they surround, particularly preferably at a flow velocity which is at least 10 m/s higher, very particularly preferably at least 20 m/s and in particular at least 50 m/s higher.

However, it can also be possible and advantageous to introduce the outer phosgene stream into the mixing space at a higher flow velocity than the amine stream and to introduce the inner phosgene stream at a lower flow velocity. This represents a further possible embodiment of the present invention.

In a preferred embodiment of the invention, it is useful to introduce the phosgene streams, in particular the outer phosgene stream, through the annular gap into the mixing space at a lower flow velocity than the amine stream which they surround, particularly preferably at a flow velocity which is at least 50 m/s lower, very particularly preferably at least 120 m/s lower, very particularly preferably 160 m/s lower and especially at least 180 m/s lower.

In a preferred embodiment of the present invention, the (n+1) annular gaps for the phosgene streams are connected to precisely one phosgene feed line so as to give a low pressure drop and without additional regulating devices, so that the velocity at which the phosgene flows out of the (n+1) annular gaps is approximately equal.

Likewise, the n annular gaps for the amine streams are preferably connected to precisely one amine feed line so as to give a low pressure drop and without additional regulating devices, so that the velocity at which the amine flows out of the n annular gaps is approximately equal.

However, it is also possible for the phosgene and/or amine streams from the annular gaps to be connected in each case to a separately regulated feed line so that the velocities per feed line can be set individually and independently of one another.

The starting materials enter the mixing space with a velocity vector. The velocity vector can be divided into an axial component, a radial component and a tangential component. The axial direction is taken to mean the component of the velocity vector parallel to the longitudinal axis of the mixing space. The radial direction is taken to mean the component of the velocity vector from outside onto the longitudinal axis, i.e. forming a right angle with the longitudinal axis. The tangential direction is taken to mean the component of the velocity vector parallel to the outer boundary of the annular gap space, i.e. a circulatory movement.

In terms of the mixing of the feed streams, an improvement in the mixing established can be achieved by installation of elements which generate a tangential velocity, for example in the feed line for the substreams of the excess components into the mixing space. A suitable tangential-velocity-generating element would be, for example, a spirally twisted ribbon (helix) inserted in the feed line, round or annular guide plates (guide vanes) or the like. The effect of the tangential-velocity-generating internals is to increase the shear between flow layers of differing composition in the flow in the nozzle.

To generate a tangential velocity, it is also possible to employ tangential entry of the feed line for one or more feed streams or, in the case of radial inflow of one or more feed streams, a blade ring.

Furthermore, it can be useful to introduce the phosgene and amine streams into the mixing space with opposite tangential velocities, for example by introducing the phosgene streams into the mixing space with a tangential velocity which is clockwise when viewed along the longitudinal axis of the reactor and introducing the amine stream located in between with a tangential velocity which is counterclockwise.

The included angle which the sum vector of the vectors of the tangential velocity and the vector of the axial velocity of the streams introduced in this way makes with the longitudinal axis of the reactor can be from 5 to 85°, preferably from 17 to 73°, particularly preferably from 30 to 60°, for the one streams, for example the phosgene streams, and from −5 to −85°, preferably from −17 to −73°, particularly preferably from −30 to −60°, for the other streams, for example the amine stream.

It is also useful to introduce the flows into the mixing space at different radial velocities. Here, the sum vector of the radial velocity vector and the axial velocity vector makes an angle with the longitudinal axis. This angle generally corresponds to the angle between the associated introduction channel and the longitudinal axis of the mixing space. Here, a negative angle means introduction from the inside outward, a positive angle means introduction from the outside inward, an angle of 0° indicates flow parallel to the longitudinal axis of the mixing space and an angle of 90° indicates flow perpendicular to the longitudinal axis of the mixing space.

The outer phosgene stream can be introduced into the mixing space at a radial angle of from 0 to 85°, preferably from 5 to 85°, particularly preferably from 7 to 65°, very particularly preferably from 15 to 35° and in particular from 18 to 30°, by means of the mixing device.

The amine stream can be introduced into the mixing space at a radial angle of from −50° to +50°, preferably from −25 to 25°, particularly preferably from −10 to 10° and very particularly preferably from −3 to +30, by means of the mixing device.

The inner phosgene stream can be introduced into the mixing space at a radial angle of from 0 to −85°, preferably from −5 to −85°, particularly preferably from −7 to −65°, very particularly preferably from −15 to −35° and in particular from −18 to −30°, by means of the mixing device.

It is advantageous for the outer phosgene stream and the amine stream to form an included radial angle of from 1 to 45°, preferably from 7 to 40, particularly preferably from 15 to 35 and particularly preferably from 18 to 30°, relative to one another.

It is also advantageous for the amine stream and the inner phosgene stream to form an included radial angle of from 1 to 45°, preferably from 10 to 40°, particularly preferably from 15 to 35° and particularly preferably from 18 to 30°, relative to one another.

Reaction Space

The reaction space comprises, in the front region, the mixing space in which the mixing of the gaseous mixture of phosgene, amine, if appropriate mixed with inert medium, predominantly takes place, which is generally accompanied by commencement of the reaction. Then, essentially only the reaction and at most a subordinate degree of mixing takes place in the back part of the reaction space.

For the purpose of making a distinction, the mixing space can be taken to be the region of the reaction space in which 99% of the mixing of the starting materials takes place. In a preferred embodiment of the present invention, the conversion in the mixing space, i.e. the consumption of the amine introduced, is less than 15%. Here, the degree of mixing is the ratio of the difference of the locally averaged mix fraction and the initial mix fraction prior to mixing to the difference of the mean final mix fraction after mixing and the initial mix fraction prior to mixing. For the concept of the mix fraction, reference may be made to, for example, J. Warnatz, U. Maas, R. W. Dibble: Verbrennung, Springer Verlag, Berlin Heidelberg N.Y., 1997, 2nd edition, p. 134.

For the purposes of the present invention, the reactor is the technical apparatus which comprises the reaction space. These can be all customary reaction spaces known from the prior art which are suitable for a noncatalytic, single-phase gas reaction, preferably for a continuous noncatalytic, single-phase gas reaction, and withstand the moderate pressures required. Suitable materials for contact with the reaction mixture are, for example, metals such as steel, tantalum, silver or copper, glass, ceramic, enamel or homogeneous or heterogeneous mixtures thereof. Preference is given to using steel reactors. The walls of the reactor can be hydraulically smooth or profiled. Suitable profiles are, for example, grooves or corrugations.

It is generally possible to use the types of reactor known from the prior art. Examples of reactors are known from EP-B1 289840, column 3, line 49-column 4, line 25, EP-B1 593334, WO 2004/026813, page 3, line 24-page 6, line 10, WO 03/045900, page 3, line 34-page 6, line 15, EP-A1 1275639, column 4, line 17-column 5, line 17, and EP-B1 570799, column 2, line 1-column 3, line 42, which are each hereby expressly incorporated by reference into the present disclosure.

Preference is given to using tube reactors.

It is likewise possible to use essentially cuboidal reaction spaces, preferably plate reactors or plate reaction spaces. A particularly preferred plate reactor has a ratio of width to height of at least 2:1, preferably at least 3:1, particularly preferably at least 5:1 and in particular at least 10:1. The upper limit to the ratio of width to height depends on the desired capacity of the reaction space and is in principle not restricted. Reaction spaces having a ratio of width to height of up to 5000:1, preferably up to 1000:1, have been found to be appropriate from an industrial point of view.

The reaction of phosgene with amine in the reaction space occurs at absolute pressures of from >0.1 bar to <20 bar, preferably from 0.5 bar to 15 bar and particularly preferably from 0.7 to 10 bar. In the case of the reaction of (cyclo) aliphatic amines, the absolute pressure is very particularly preferably from 0.7 bar to 5 bar, in particular from 0.8 to 3 bar and especially from 1 to 2 bar.

The pressure in the feed lines to the mixing device is generally higher than the above-mentioned pressure in the reactor. Depending on the choice of mixing device, this pressure drops. The pressure in the feed lines is preferably from 20 to 2000 mbar higher, particularly preferably from 30 to 1000 mbar higher, than in the reaction space.

In one possible embodiment, the reactor comprises a bundle of reactors. In one possible embodiment, the mixing unit does not have to be an independent device; rather, it can be advantageous to integrate the mixing unit into the reactor. An example of an integrated unit made up of mixing unit and reactor is a tube reactor having flanged-on nozzles.

In the process of the present invention, the reaction of phosgene with amine occurs in the gas phase. For the purposes of the present invention, the expression "reaction in the gas phase" means that the conversion of the feed streams and intermediates into the products occurs in the gaseous state and during the reaction at least 95%, preferably at least 98%, particularly preferably at least 99%, very particularly preferably at least 99.5%, in particular at least 99.8% and especially at least 99.9%, of these components remain in the gas phase during passage through the reaction space.

Intermediates are, for example, the monoaminomonocarbamoyl chlorides, dicarbamoyl chlorides, monoaminomonoisocyanates and monoisocyanatomonocarbamoyl chlorides formed from the diamines and also the hydrochlorides of the amino compounds.

In the process of the invention, the temperature in the reaction space is selected so that it is above the boiling point of the diamine used, based on the pressure conditions prevailing in the reaction space. Depending on the amine used and the pressure set, the temperature in the reaction space is advantageously more than 200° C., preferably more than 260° C. and particularly preferably more than 300° C. The temperature is generally up to 600° C., preferably up to 570° C.

The mean contact time of the reaction mixture in the process of the invention is generally in the range from 0.001 second to <5 seconds, preferably from >0.01 second to <3 seconds, particularly preferably from >0.015 second to <2 seconds. In the case of (cyclo)aliphatic amines, the mean contact time in the reaction is very particularly preferably from 0.015 to 1.5 seconds, in particular from 0.015 to 0.5 second, especially from 0.020 to 0.1 second and often from 0.025 to 0.05 second.

For the purposes of the present invention, the mean contact time is the period of time from when mixing of the starting materials commences until the products leave the reaction space and go to the work-up stage. In a preferred embodiment, the flow in the reactor of the process of the invention has a Bodenstein number of more than 10, preferably more than 100 and particularly preferably more than 500.

In a preferred embodiment, the dimensions of the reaction space and the flow velocities are selected so that the reaction mixture displays turbulent flow, i.e. flow at a Reynolds number of at least 2300, preferably at least 2700, with the Reynolds number being calculated on the basis of the hydraulic diameter of the reaction space.

The gaseous reaction mixture preferably passes through the reaction space at a flow velocity of from 10 to 300 meter/second, preferably from 25 to 250 meter/second, particularly preferably from 40 to 230 meter/second, very particularly preferably from 50 to 200 meter/second, in particular from >150 to 190 meter/second and especially from 160 to 180 meter/second.

Due to the turbulent flow, narrow residence time distributions having a low standard deviation of usually not more than 6% as described in EP 570799 and good mixing are achieved. Measures such as the constriction described in EP-A-593 334, which is also susceptible to blockages, are not necessary.

It can be useful to install flow equalizers as are known, for example, from EP 1362847 A in the reactor.

The reaction volume can be heated/cooled via its outer surface. To build production plants having a high plant capacity, a plurality of reactor tubes can be connected in parallel. However, it can also be preferred to carry out the reaction adiabatically. This means that heating or cooling energy flows do not occur via the outer surface of the reaction volume as a result of engineering measures.

In a preferred embodiment, the reaction conditions are selected so that the reaction gas at the outlet from the reaction space has a phosgene concentration of more than 25 mol/m$^3$, preferably from 30 to 50 mol/m$^3$. Furthermore, the inert medium concentration at the outlet from the reaction space is generally more than 25 mol/m$^3$, preferably from 30 to 100 mol/m$^3$.

The reaction space can essentially be divided structurally into up to four longitudinal sections along the longitudinal axis of the reactor over the course of the flow:

a first, usually short section downstream of the feed device for the starting materials having a length $L_1$,
a second section having a length $L_2$,
a third section having a length $L_3$ followed by
a fourth section having a length $L_4$ which represents a tube reactor without internal displacement bodies and is followed by a quench (see below).

The reaction space is, for the present purposes, the volume in which at least 98% of the conversion, i.e. the consumption of the amine introduced, preferably at least 99%, particularly preferably 99.5%, very particularly preferably 99.7%, in particular 99.9% and especially 99.99%, takes place.

The individual parameters which describe the geometries in these up to four sections are denoted by the indices 1, 2, 3 and 4.

The main characterizing parameters are the total diameter R of the tube reactor, i.e. from interior wall to interior wall including the volume body present in the reactor, and the external diameter r of this volume body.

Further characterizing parameters are the angles $\alpha$ and $\beta$, of which $\alpha$ is the angle made by the outer wall with the longitudinal axis of the tube reactor and $\beta$ is the angle made by the volume body with the longitudinal axis of the tube reactor.

A positive angle $\alpha$ thus indicates a widening of the outer wall of the tube reactor in the flow direction, and, on the other hand, a negative angle $\alpha$ indicates a narrowing.

A negativer angle $\beta$ analogously indicates a volume body which narrows in the flow direction, and a positive angle $\beta$ indicates a widening volume body.

The parameters R and r indirectly determine the area F of the reactor through which flow occurs, and $\alpha$ and $\beta$ indicate how they change in the flow direction.

At the transitions from one section to another, the values of R and r can coincide or can change so as to lead to a sudden widening/narrowing.

The present invention further provides various preferred constructions of the reaction space which differ in the size of the cross-sectional areas along the longitudinal axis of the reactor during the course of flow:

In the first alternative construction, the area F through which flow occurs does not change along the reactor, i.e. there is no structural difference between sections but instead there is only a single section 1. In this section, $r_1$ and $R_1$ remain constant over the entire length of the reactor, and $\alpha_1$ and $\beta_1$ are each 0°. The entire reactor is thus formed by one annular gap space, preferably a rotationally symmetric annular gap space, particularly preferably a hollow cylinder.

In a second alternative construction, the area $F_1$ through which flow occurs increases in a section 1 and then remains constant in a second section 2.

This is preferably achieved by keeping $R_1$ constant and reducing $r_1$ along section 1 to a value of zero. The angle $\alpha_1$ is then 0° and the angle $\beta_1$ is from −1 to −10°, preferably from −2 to −8°, particularly preferably from −3 to −7° and very particularly preferably from −4 to −6°. However, the angle $\alpha_1$ can also vary along section 1.

The length $L_1$ can be calculated from the diameter $r_1$ at the beginning of section 1 and the angle $\beta_1$ in a simple trigonometric calculation.

In section 2, $R_2$ remains constant and $r_2$ is zero, and $\alpha_2$ and $\beta_2$ are each 0°.

The second alternative construction can also be achieved by increasing $R_1$ and keeping $r_1$ constant. In this case, the angle $\beta_1$ is 0° and the angle $\alpha_1$ is from 0.0001 to 10°, preferably from 0.0002 to 8°, particularly preferably from 0.0003 to 7° and very particularly preferably from 0.0003 to 6°.

In section 2, $R_2$ and $r_2$ then remain constant, and $\alpha_2$ and $\beta_2$ are each 0°. In a third alternative construction, the area $F_1$ remains constant in a section 1 and increases in the second section and again remains constant in the third section.

To achieve this, $R_1$ and $r_1$ remain constant and $\alpha_1$ and $\beta_1$ are each 0° in section 1.

In the second section, $F_2$ increases, which is achieved by an increasing $R_2$ and a constant $r_2$. This means that $\beta_2$ is zero and $\alpha_2$ is, for example, from 0.0001 to 10°, preferably from 0.0002 to 8°, particularly preferably from 0.0003 to 7° and very particularly preferably from 0.0003 to 6°.

In the third section, $F_3$ remains constant, which is achieved by $R_3$ and $r_3$ remaining constant, $\alpha_3$ and $\beta_3$ each being 0°.

As an alternative, this third alternative construction can also be achieved by $R_2$ being kept constant and $r_2$ being reduced to zero in the second section. The angle $\alpha_2$ is then 0° and the angle $\beta_2$ is from −1 to −10°, preferably from −2 to −8°, particularly preferably from −3 to −7° and very particularly preferably from −4 to −6°.

The constant area in sections 1 and 3 is once again achieved by keeping $R_1$ and $r_1$ constant and keeping $R_3$ and $r_3$ constant.

In a fourth alternative construction, the area $F_1$ is kept constant in a section 1, $F_2$ is then reduced in section 2 and $F_3$ is increased in section 3 and is kept constant in section 4.

This is achieved by keeping $R_1$ and $r_1$ constant and keeping each of $\alpha_1$ and $\beta_1$ at 0°.

In the second section, $F_2$ decreases, which is achieved by a decreasing $R_2$ and a constant $r_2$. For this purpose, $\beta_2$ is kept at 0°, and $\alpha_2$ is, for example, less than 0° and more than −90°, preferably from −7 to −65°, particularly preferably from −15 to −35° and very particularly preferably from −20 to −30°.

In the third section, $F_3$ increases, which is achieved by an increasing $R_3$ and a constant $r_3$, which means that $\beta_3$ is zero and $\alpha_3$ is, for example, from 0.0001 to 10°, preferably from 0.0002 to 8°, particularly preferably from 0.0003 to 7° and very particularly preferably from 0.0003 to 6°.

In the fourth section, $F_4$ then remains constant, for which purpose $R_4$ and $r_4$ remain constant and $\alpha_4$ and $\beta_4$ are each 0° in section 4.

As an alternative, this fourth alternative construction can also be achieved as follows:

$R_1$ and $r_1$ are kept constant and $\alpha_1$ and $\beta_1$ are each kept at 0° (constant $F_1$).

In the second section, $F_2$ decreases, which is achieved by a decreasing $R_2$ and a constant $r_2$. For this purpose, $\beta_2$ is kept at 0°, and $\alpha_2$ is, for example, less than 0° and more than −90°, preferably from −7 to −65°, particularly preferably from −15 to −35° and very particularly preferably from −20 to −30°.

In contrast, the reduction in the area $F_3$ in the third section is achieved by an $r_3$ which decreases to zero and a constant $R_3$. The angle $\alpha_3$ is then 0° and the angle $\beta_3$ is from −1 to −10°, preferably from −2 to −8°, particularly preferably from −3 to −7° and very particularly preferably from 4 to −6°.

In the fourth section, $R_4$ is kept constant and $r_4$=0. $\alpha_4$ and $\beta_4$ are each 0°.

In a fifth alternative construction, the area $F_1$ is decreased in the first section, $F_2$ is increased in the second section and $F_3$ is kept constant in the third section.

In the first section, $F_1$ decreases, which is achieved by a decreasing $R_1$ and a constant $r_1$. For this purpose, $\beta_1$ is kept at 0°, and $\alpha_1$ is, for example, less than 0° and more than −90°, preferably from −7 to −65°, particularly preferably from −15 to −35° and very particularly preferably from −20 to −30°.

In the second section, $F_2$ increases, which is achieved by an increasing $R_2$ and a constant $r_2$, which means that $\beta_2$ is zero and $\alpha_2$ is, for example, from 0.0001 to 10°, preferably from 0.0002 to 8°, particularly preferably from 0.0003 to 7° and very particularly preferably from 0.0003 to 6°.

In section 3, $R_3$ and $r_3$ remain constant, $\alpha_3$ and $\beta_3$ are each 0°.

In an alternative embodiment, the fifth alternative construction, the configuration can be as follows:

In the first section, $F_1$ decreases, which is achieved by a decreasing $R_1$ and a constant $r_1$. For this purpose, $\beta_1$ is kept at 0°, and $\alpha_1$ is, for example, less than 0° and more than −90°, preferably from −7 to −65°, particularly preferably from −15 to −35° and very particularly preferably from −20 to −30°.

The reduction in the area $F_2$ is now achieved by keeping $R_2$ constant in the second section and decreasing $r_2$ to zero. The angle $\alpha_2$ is then 0° and the angle $\beta_2$ is from −1 to −10°, preferably from −2 to −8°, particularly preferably from −3 to −7° and very particularly preferably from −4 to −6°.

In section 3, $R_3$ and $r_3$ remain constant, with $R_3=R_2$ and $r_3=0$, $\alpha_3$ and $\beta_3$ each being 0°.

In the sixth alternative construction, the area $F_1$ is reduced, remains constant in section two, is increased again in section 3 and then remains constant again in the fourth section.

In the first section, $F_1$ decreases, which is achieved by a decreasing $R_1$ and a constant $r_1$. For this purpose, $\beta_1$ is kept at 0°, and $\alpha_1$ is, for example, less than 0° and more than −90°, preferably from −7 to −65°, particularly preferably from −15 to −35° and very particularly preferably from −20 to −30°.

In section 2, $R_2$ and $r_2$ remain constant, and $\alpha_2$ and $\beta_2$ are each 0°.

In the third section, $F_3$ increases, which is achieved by an increasing $R_3$ and a constant $r_3$ which is also equal to $r_2$, which means that $\beta_3$ is zero and $\alpha_3$ is, for example, from 0.0001 to 10°, preferably from 0.0002 to 8°, particularly preferably from 0.0003 to 7° and very particularly preferably from 0.0003 to 6 °.

In section 4, $R_4$ and $r_4$ remain constant, $\alpha_4$ and $\beta_4$ are each 0°.

In an alternative embodiment of the sixth alternative construction, the configuration can be as follows:

In the first section, $F_1$ decreases, which is achieved by a decreasing $R_1$ and a constant $r_1$. For this purpose, $\beta_1$ is kept at 0°, and $\alpha_1$ is, for example, less than 0° and more than −90°, preferably from −7 to −65°, particularly preferably from −15 to −35° and very particularly preferably from −20 to −30°.

In section 2, $R_2$ and $r_2$ remain constant, and $\alpha_2$ and $\beta_2$ are each 0°.

The reduction in the area $F_3$ is now achieved by keeping $R_3$ constant in the third section and reducing $r_3$ to zero. The angle $\alpha_3$ is then 0° and the angle $\beta_3$ is from −1 to −10°, preferably from −2 to −8°, particularly preferably from −3 to −7° and very particularly preferably from −4 to −6°.

In section 4, $R_4$ and $r_4$ remain constant, with $R_4=R_3$ and $r_4=0$, $\alpha_4$ and $\beta4$ each being 0°.

In the sixth alternative construction, the length of section 2 is selected differently depending on the amine used: in the case of isocyanates which have a strong tendency to form deposits, e.g. (cyclo)aliphatic isocyanates and in particular hexamethylene 1,6-diisocyanate, a short section 2 is preferred.

The length $L_2$ of zone 2 is generally less than 30 times the resulting gap width ($R_2-r_2$), preferably less than 15 times, particularly preferably less than 10 times, very particularly preferably less than 6 times, in particular less than five times and especially less than three times, the gap width. $L_2$ is often less than twice the gap width ($R_2-r_2$) and even less than once the gap width.

On the other hand, a long section 2 is preferred in the case of isocyanates which have a low tendency to form deposits, for example aromatic isocyanates and in particular tolylene diisocyanate.

In the case of such isocyanates, the length of zone 2 is greater than once the resulting gap width ($R_2-r_2$), preferably greater than 5 times, particularly preferably greater than 10 times, very particularly preferably greater than 15 times and especially greater than 30 times, the gap width.

The length of the last section having a constant area F in each case, i.e. $L_4$ in the sixth alternative construction, is selected so that, firstly, the desired mean contact time in the reactor is achieved and, secondly, an $L_4/(2*R_4)$ ratio of greater than 2, preferably greater than 4, particularly preferably greater than 6, very particularly preferably greater than 10 and especially greater than 15, is obtained.

In sections having a constant or increasing area, F is selected so that the mean velocity of the reaction mixture is generally greater than 60 m/s, preferably greater than 100 m/s, particularly preferably greater than 160 m/s and very particularly preferably greater than 180 m/s and especially greater than 200 m/s. In addition, F is selected so that the mean velocity is generally less than 250 m/s, preferably less than 240 m/s, particularly preferably less than 230 m/s, very particularly preferably less than 220 m/s and especially less than 210 m/s.

The changes in the parameters R and r within the sections can be linear or nonlinear. In the case of a linear change, the angles $\alpha$ and $\beta$ remain constant within the sections and change only at the transitions between the sections. In the case of a nonlinear profile within the sections, the shape can be concave, i.e. bending into the flow space, convex, i.e. bending away from the flow space, or mixed concave-convex or convex-concave. A concave shape means that the angle $\alpha$ increases or becomes more positive during the course of the flow and the angle $\phi$ becomes smaller or more negative. Preference is given to a linear change.

The transitions between the respective sections 1 to 4 can, independently of one another, be steps or rounded. Preference is given to a rounded configuration.

Figure 2:
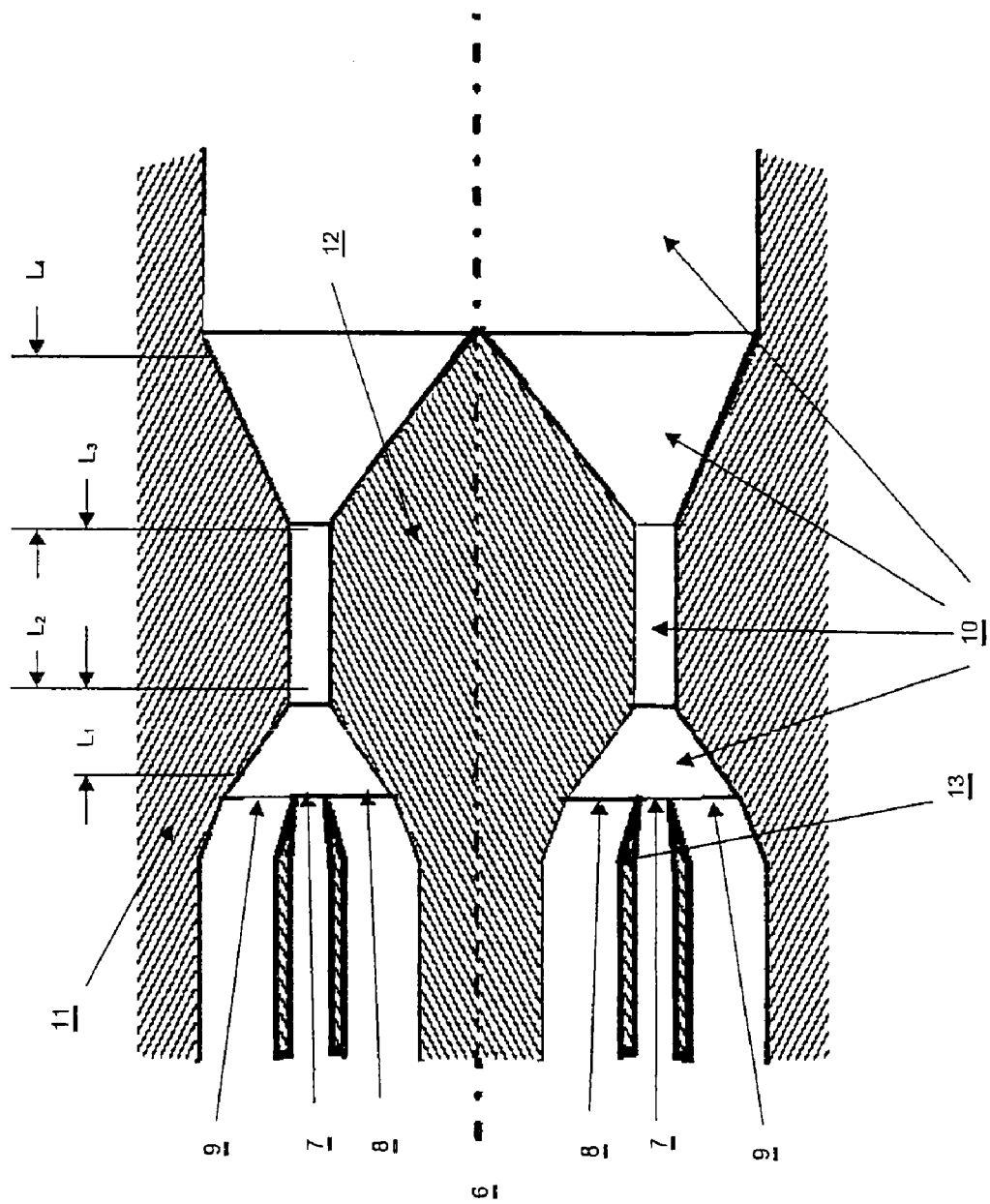
FIG. 2 shows one embodiment of the reactor.

A particularly preferred embodiment of the sixth alternative construction is shown in FIG. 2 (not to scale):

A circular annular gap 7 for introduction of the amine and an inner circular annular gap 8 plus an outer circular annular gap 9 for introduction of phosgene are arranged in a rotationally symmetric fashion around an imaginary axis 6. The reaction space 10 is bounded by an outer reactor wall 11 and an internal volume body 12 and divided along the course of the reaction into four sections having lengths $L_1$, $L_2$, $L_3$ and $L_4$ which differ in terms of the area through which flow occurs in them. Along the first section, immediately after mixing of the feed streams, the area $F_1$ through which flow occurs is decreased by decreasing $R_1$ and increasing $r_1$, remains constant in section 2, increases again in section 3 as a result of an increasing $R_3$ and an $r_3$ decreasing to a value of zero, and then remains constant in the fourth section.

The volume body in the interior of the tube reactor is preferably connected to the walls of the reactor to stabilize the body, preferably by means of struts or guide plates. The shape of these struts is preferably very streamlined, for example having a teardrop-shaped cross section. However, it is also possible to use these fastening devices to achieve an additional increase in the tangential velocity of the reaction mixture, leading to additional mixing.

The volume of the reactor through which flow occurs can be filled with static mixers, for example packing, shaped bodies, woven fabrics, perforated or slotted metal sheets, but the volume is preferably very largely free of internals.

The installation of guide plates in the reaction space is also conceivable. A suitable turbulence-generating element would be, for example, an installed spirally twisted ribbon, round or angular inclined plates or the like.

After the reaction, the gaseous reaction mixture is preferably scrubbed with a solvent at temperatures above 130° C. (quench). As solvents, preference is given to using hydrocarbons which may optionally be substituted with halogen atoms, for example hexane, benzene, nitrobenzene, anisole, chlorobenzene, chlorotoluene, o-dichlorobenzene, trichlorobenzene, diethyl isophthalate (DEIP), tetrahydrofuran (THF), dimethylformamide (DMF), xylene, chloronaphthalene, decahydronaphthalene and toluene. Monochlorobenzene is particularly preferably used as solvent. It is also possible to use the isocyanate as solvent. In the scrub, the isocyanate is selectively transferred to the scrubbing solution. The remaining gas and the scrubbing solution obtained are subsequently separated into isocyanate, solvent, phosgene and hydrogen chloride, preferably by means of rectification.

After the reaction mixture has been reacted in the reaction space, it is passed to the work-up apparatus in which the quench is carried out. This is preferably a scrubbing tower in which the isocyanate formed is separated off from the gaseous mixture by condensation in an inert solvent, while excess phosgene, hydrogen chloride and, if appropriate, the inert medium pass in gaseous form through the work-up apparatus. The temperature of the inert solvent is preferably kept above the dissolution temperature of the carbamoyl chloride corresponding to the amine in the quenching medium chosen. The temperature of the inert solvent is particularly preferably kept above the melting point of the carbamoyl chloride corresponding to the amine.

In general, the pressure in the work-up apparatus is lower than in the reaction space. The pressure is preferably from about 50 to 500 mbar lower, particularly preferably from 80 to 150 mbar lower, than in the reaction space.

The scrub can, for example, be carried out in a stirred vessel or in other conventional apparatuses, e.g. in a column or mixer-settler apparatus.

In process engineering terms, all extraction and scrubbing processes and apparatuses which are known per se, e.g. those described in Ullmann's Encyclopedia of Industrial Chemistry, 6th ed, 1999 Electronic Release, chapter: Liquid-Liquid Extraction—Apparatus, can be used for a scrub in the process of the invention. These can be, for example, single-stage or multistage, preferably single-stage, extractions, and also those carried out in cocurrent or countercurrent, preferably countercurrent.

A suitable quench is known, for example, from EP-A1 1403248, column 2, line 39-column 3, line 18, which is hereby expressly incorporated by reference into the present disclosure.

In this quenching zone, the reaction mixture, which consists essentially of the isocyanates, phosgene and hydrogen chloride, is intensively mixed with the liquid sprayed in. Mixing is carried out so that the temperature of the reaction mixture is decreased from an initial 200 to 570° C. to 100 to 200° C., preferably to 140-180° C., and the isocyanate comprised in the reaction mixture goes over wholly or partly into the liquid droplets as a result of condensation, while the phosgene and the hydrogen chloride remain essentially completely in the gas phase.

The proportion of the isocyanate comprised in the gaseous reaction mixture which goes over into the liquid phase in the quenching zone is preferably from 20 to 100% by weight, particularly preferably from 50 to 99.5% by weight and in particular from 70 to 99% by weight, based on the isocyanate comprised in the reaction mixture.

The reaction mixture preferably flows through the quenching zone from the top downward. Below the quenching zone, there is a collection vessel in which the liquid phase is precipitated, collected and removed from the reaction space via an outlet and is subsequently worked up. The remaining gas phase is removed from the reaction space via a second outlet and is likewise worked up.

The quench can, for example, be carried out as described in EP 1403248 A1 or as described in the unpublished International Application number PCT/EP/05/006745, filed on Jun. 22, 2005.

The liquid droplets are, for this purpose, produced by means of single-fluid or two-fluid atomizer nozzles, preferably single-fluid atomizer nozzles, and, depending on the configuration, form a spray cone angle of from 10 to 140°, preferably from 10 to 120°, particularly preferably from 10° to 1000°.

The liquid which is sprayed in via the atomizer nozzles has to have a good solvent capability for isocyanates. Preference is given to using organic solvents. Particular preference is given to using aromatic solvents which may be substituted by halogen atoms.

In a particular embodiment of the process, the liquid which is sprayed in is a mixture of isocyanates, a mixture of isocyanates and solvent or isocyanate, with the quenching liquid used in each case being able to comprise proportions of low boilers such as HCl and phosgene. Preference is given to using the isocyanate which is prepared in the respective process. Since the reaction is stopped by the temperature decrease in the quenching zone, secondary reactions with the isocyanates sprayed in can be ruled out. The advantage of this embodiment is, in particular, that removal of the solvent can be dispensed with.

In an alternative preferred embodiment, the inert medium which is used together with at least one of the starting materials and the solvent used in the quench are the same compound. In this case, particular preference is given to using monochlorobenzene.

Small amounts of by-products which remain in the isocyanate can be separated from the desired isocyanate by means of additional rectification, by stripping with an inert gas or by crystallization, preferably by rectification.

In the subsequent optional purification stage, the isocyanate is separated from the solvent, preferably by distillation. The removal of remaining impurities comprising hydrogen chloride, inert medium and/or phosgene can likewise be carried out here, as described, for example, in DE-A1 10260092.

The present invention further provides an apparatus comprising at least one tube reactor whose one end face is provided with (2n+1) annular gaps arranged in a circular fashion around one another, where n is a positive integer of at least 1, preferably 1, 2 or 3, particularly preferably 1 or 2 and very particularly preferably 1, of which each second annular gap is connected to at least one feed line for a feed stream and the annular gaps located in between are connected to at least one feed line for another feed stream, with the annular gaps being preferably arranged concentrically, particularly preferably rotationally symmetrically concentrically, around the longitudinal axis of the reactor at the end face and a volume body which is arranged around the longitudinal axis of the reactor and projects into the tube reactor being located in the middle thereof, with the external diameter of the volume body and the internal diameter of the tube reactor enclosing a reaction space.

The cross-sectional area of the reaction space enclosed between the interior wall of the tube reactor and the outer wall of the volume body can preferably be constructed as described in the above-described alternative constructions.

In addition, the opposite end face of the tube reactor can be provided with a connection to a further apparatus in which there is at least one atomizer nozzle by means of which a liquid can be brought into contact with the reaction mixture leaving the tube reactor.

In a preferred embodiment of the present invention, the apparatus can be configured so that the feed lines for the feed streams, preferably the amine streams, narrow at the transition to the annular gaps in the direction of the annular gaps (13 in FIG. 2) and the walls of the feed lines taper at a half opening angle, i.e. the angle between the longitudinal axis of the feed line and the narrowing wall of the feed line, of from >0° up to and including 70°, preferably from 1 to 60°, particularly preferably from 2 to 50°, particularly preferably from 3 to 45°, very particularly preferably from 5 to 40, in particular from 7 to 30 and especially from 7 to 20°.

The length of the narrowing is determined by the angle selected and the external diameter of the annular gap and the internal diameter of the feed pipe.

Mixing of the various streams with little deposition of solids is achieved by means of such narrowing and angles.

The invention claimed is:

1. A process for preparing an isocyanate, comprising reacting, in the gas phase, an amine with phosgene, in the presence of an inert medium,
   wherein
   n amine streams are reacted with n+1 phosgene streams in a reactor,
   n is a positive integer of at least 1,
   all amine and phosgene streams are introduced into a mixing space through annular gaps,
   mixing of the n amine streams and the n+1 phosgene streams occurs in the mixing space, which comprises an annular gap space for mixing, and
   an interior of the annular gap space for mixing is filled out by an internal displacement body.

2. The process according to claim 1, wherein the isocyanate is at least one selected from the group consisting of 1,6-diisocyanatohexane, 1-isocyanato-3,3,5-trimethyl-5-(isocyanatomethyl)cyclohexane, 4,4'-di(isocyanatocyclohexyl)methane and tolylene diisocyanate isomer mixtures.

3. The process according to claim 1, wherein the inert medium is at least one selected from the group consisting of nitrogen, helium, argon, chlorobenzene, chlorotoluene, o-dichlorobenzene, toluene, xylene, chloronaphthalene, decahydronaphthalene, carbon dioxide and carbon monoxide.

4. The process according to claim 3, wherein a gas volume of inert medium to amine or to phosgene is from >0.0001 to 30.

5. The process according to claim 1, wherein the temperature in the process is from 200 to 600° C.

6. The process according to claim 1, wherein a molar ratio of phosgene to amino groups is from 1.1:1 to 20:1.

7. The process according to claim 1, wherein an outermost stream introduced into the mixing space at an outer wall and an innermost stream introduced into the mixing space are each a phosgene stream.

8. The process according to claim 1, wherein:
   each amine stream is introduced into the mixing space between two respective phosgene streams; and
   a ratio of the area of a respective outer phosgene stream, to the area of an amine stream, to the area of a respective adjacent inner phosgene stream is 0.3-5:1:0.3-5.

9. The process according to claim 1, wherein a ratio of the total area of the n amine streams to the total area of the n+1 phosgene streams is greater than 0.00002 and less than 5.

10. The process according to claim 1, wherein individual starting materials are conveyed in a mixing device at a flow velocity of from 20 to 400 meter/second into the mixing space.

11. The process according to claim 1, wherein the reactor, in which the reaction occurs, comprises an annular gap space for reaction.

12. The process according to claim 11, wherein an interior of the annular gap space for reaction comprises a volume body to form the annular gap space for reaction.

13. The process according to claim 12, wherein the volume body tapers to a diameter of zero along the reactor.

14. The process according to claim 11, wherein the area of the reactor through which flow occurs does not change during passage through the reactor.

15. The process according to claim 11, wherein the area of the reactor through which flow occurs increases in a first section during passage through the reactor and subsequently remains constant in a second section.

16. The process according to claim 11, wherein the area of the reactor through which flow occurs remains constant in a first section during passage through the reactor, increases in a second section and remains constant in a third section.

17. The process according to claim 11, wherein the area of the reactor through which flow occurs remains constant in a first section during passage through the reactor, decreases in a second section, increases in a third section and remains constant in a fourth section.

18. The process according to claim 11, wherein the area of the reactor through which flow occurs decreases in a first section during passage through the reactor, increases in a second section and remains constant in a third section.

19. The process according to claim 11, wherein the area of the reactor through which flow occurs decreases in a first section during passage through the reactor, remains constant in a second section, increases in the third section and remains constant in a fourth section.

20. The process according to claim 1, wherein a mean contact time of a reaction mixture is from 0.001 seconds to <5 seconds.

21. The process according to claim 1, wherein a flow in the reactor has a Bodenstein number of more than 10.

22. The process according to claim 1, wherein a flow of a reaction mixture has a Reynolds number of least 2300.

23. The process according to claim 1, wherein the conversion of amine, in a space in which mixing of the starting materials takes place to a degree of 99%, is not more than 15%.

* * * * *